United States Patent
Zhang et al.

(10) Patent No.: US 9,931,476 B2
(45) Date of Patent: Apr. 3, 2018

(54) DISPOSABLE SAFETY SELF-DESTRUCTION INSULIN NEEDLE

(71) Applicant: Beipu Medical Technology Co.,Ltd., Wenzhou (CN)

(72) Inventors: Hongjie Zhang, Wenzhou (CN); Linfeng Zhang, Wenzhou (CN)

(73) Assignee: Beipu Medical Technology Co., Ltd., Wenzhou (CN)

( * ) Notice: Subject to any disclaimer, the term of this patent is extended or adjusted under 35 U.S.C. 154(b) by 82 days.

(21) Appl. No.: 14/929,407

(22) Filed: Nov. 1, 2015

(65) Prior Publication Data

US 2016/0121055 A1    May 5, 2016

(30) Foreign Application Priority Data

Nov. 4, 2014   (CN) ................. 2014 2 0651240 U (51) Int. Cl.
*A61M 5/32*   (2006.01)
*A61M 5/50*   (2006.01)

(52) U.S. Cl.
CPC ........ *A61M 5/3278* (2013.01); *A61M 5/3202* (2013.01); *A61M 5/326* (2013.01); *A61M 5/50* (2013.01); *A61M 2005/3247* (2013.01); *A61M 2005/3267* (2013.01); *A61M 2005/3282* (2013.01); *A61M 2005/3284* (2013.01)

(58) Field of Classification Search
CPC .. A61M 2005/3267; A61M 2005/3284; A61M 2005/3279
See application file for complete search history.

(56) References Cited

U.S. PATENT DOCUMENTS

| | | | | |
|---|---|---|---|---|
| 5,053,010 A * | 10/1991 | McGary | ............. | A61M 5/3234 604/110 |
| 6,843,781 B2 * | 1/2005 | Alchas | ................. | A61M 5/326 604/117 |
| 2001/0056263 A1 * | 12/2001 | Alchas | ................... | A61M 5/46 604/193 |
| 2010/0262119 A1 * | 10/2010 | Schraga | ............. | A61M 5/3234 604/506 |
| 2010/0286609 A1 * | 11/2010 | Mahurkar | ........... | A61M 5/3234 604/110 |
| 2013/0144222 A1 * | 6/2013 | Kawamura | ....... | A61M 5/31515 604/228 |
| 2014/0221924 A1 * | 8/2014 | Hiles | .................. | A61M 5/3257 604/110 |
| 2014/0257190 A1 * | 9/2014 | Yue | .................. | A61M 37/0015 604/173 |

FOREIGN PATENT DOCUMENTS

CN           2882649 Y        3/2007

* cited by examiner

*Primary Examiner* — Imani Hayman
*Assistant Examiner* — Tezita Watts
(74) *Attorney, Agent, or Firm* — Gokalp Bayramoglu (57) ABSTRACT

The present invention discloses a disposable safety self-destruction insulin needle. The invention uses a sleeve-connected linkage structure and realizes an instant reset of the safety sleeve by means of the spring located in the middle axis so as to ensure that the needle tube is not exposed and preferably realizes a tilting and deflection of the self-destruction pressure base due to a plurality of flexible plates unevenly distributed on the inner wall in the needle base so as to finally ensure that the insulin needle cannot be used a second time, in so doing the safety self-destruction operation of the insulin needle is realized.

5 Claims, 6 Drawing Sheets

DISPOSABLE SAFETY SELF-DESTRUCTION INSULIN NEEDLE

TECHNICAL FIELD

The present invention relates to a technical field of an insulin syringe, in particular, a disposable safety self-destruction insulin syringe, in particular a mechanism thereof.

BACKGROUND

Document 1 whose patent N.O. is CN200620038771.0 and whose application date is 2006, Jan. 6, whose publication N.O. is CN2882649Y and whose publication date is 2007, Mar. 28, whose applicant is Wenzhoushi BeiPu Technology Limited Finn, discloses a needle for injection of insulin. The independent claim in Document 1 recites: it mainly comprises a needle base which is provided on the top end thereof with a needle tube, characterized in that the needle base is provided in the chamber thereof with an inner screw and has a diameter of 5 mm-50 mm, the needle tube is fitted over by a needle tube protection sleeve, the needle base is fitted over by a needle seat protection sleeve under an opening of which is provided with a dialysis paper.

The document discloses a conventional mechanism of an insulin injection needle, when using the conventional insulin syringe and pen-type insulin syringe, the needle point is exposed always in the air and therefore the problem with safety is caused apparently and the current insulin syringe has a defect inner structure which causes a result of repeatedly utilization of it after collection of it and hence a safety risk is left for a medical accident.

SUMMARY OF THE INVENTION

The invention has a purpose of providing a disposable safety self-destruction insulin needle which realizes an effective protection of the needle tube end and avoids the exposure of the needle tube after injection by utilizing supporting force of the inner elastic parts and enables the inner self-destruction pressure seat to be naturally tilted to one side after the inner self-destruction pressure seat is clamped by tactfully using asymmetrical distribution of the clamping parts so that the linkage assembly structure in the insulin needle is completely destroyed and cannot be resumed to the prior-to-use state, the self-destruction pressure seat after tilt is stuck within the insulin needle and abuts downward against the needle tube substrate and abuts upward against the safety sleeve so that the self-destruction of the insulin needle is realized and the reuse of the insulin needle is prevented. Therefore, the invention avoids all the latent safety risks and overcomes the defects and disadvantages existing in the prior art.

To fulfill the above mentioned purposes, the invention proposes a solution as follows: a disposable safety self-destruction insulin needle, it comprises a body of the insulin needle, characterized in that the body of the insulin needle is provided with a needle base therein, which is generally in a form of cylinder and which has a hollow chamber which is provided with needle tube substrate therein dividing the needle base into an upper separate space and a lower separate space that is provided on the inner wall with an inner screw, the needle tube substrate is provided on the center position of the upper surface with a spring holding post whose lower portion is located in the upper separate space, the needle tube substrate is provided with a needle tube which penetrates the needle tube substrate, one end of the needle tube extends upward followed by penetrating the spring holding post located on the centre position of the needle tube substrate, the other end of the needle tube extends towards inside of the lower separate space followed by penetrating the needle tube substrate, the two ends of the needle tube each are in form of a spine, the needle tube is provided on the inner wall of the upper separate space thereon with at least one spring plate which is located diagonally on the inner wall of the inner chamber of the needle tube and one end of which is connected to the inner wall of the inner chamber of the needle tube and the other end of which suspends in the air, the suspending end points to the upper surface of the needle tube substrate at the place close to the center position, the spring holding post is fitted over by a spring on the outside, one end of the spring abuts downward against the upper surface of the needle tube substrate, the other end of the spring upward abuts against safety sleeve, the upper end of the needle base is fitted over by a safety clamping seat the lower end of which fits within the upper end of the needle base each other, the upper end of the safety clamping seat is provided with a safety sleeve and the safety clamping seat is shaped as a general cylinder and has a hollow chamber and is provided on the inner edge of the upper opening with an annular limiting part, the safety sleeve is shaped as a cylinder and has a hollow chamber and is provided on the outer edge of the lower opening with an annular limiting protruded part cooperating to the annular limiting part, the annular limiting protruded part is located within the chamber of the safety clamping seat under the annular limiting part, the upper end surface of the annular limiting protruded part abuts downward against the lower end surface of the annular limiting part, the outer edge of the lower opening of the safety sleeve limit and fit within the inner edge of the upper opening of the safety clamping seat, the spring is fitted over by a self-destruction pressure base which is shaped as a general cylinder and has a hollow chamber, the outer diameter of the upper portion of the self-destruction base is smaller than the outer diameter of the lower portion of the self-destruction base, an annular step-shaped protrusion is formed between the upper portion and the lower portion of the self-destruction pressure seat, the outer diameter of the lower portion of the self-destruction pressure seat is larger than the diameter of the inner chamber of the safety sleeve, the outer diameter of the upper portion of the self-destruction pressure seat is smaller or equal to the diameter of the inner chamber of the safety sleeve, the upper portion of the self-destruction pressure seat is located in the chamber of the safety sleeve, the annular step-shaped protrusion has an end surface which abuts against the end surface of the lower end of the safety sleeve, the outer wall of the lower portion of the self-destruction pressure seat is provided with an annular lump cooperating with the spring plate, the vertical distance between the annular lump and the needle tube is larger than the vertical distance between the suspending part of the spring plate and the needle tube, the upper end of the safety sleeve is in a closed form, the closed end is provided with a round hole therein, the diameter of which is smaller than the diameter of the upper end of the spring, the spring has an upper end abutting upward against the inner surface of the upper end surface of the safety sleeve, the end surface of the lower end of the needle base is covered with a dialysis paper.

The invention discloses a disposable safety self-destruction insulin needle which uses a socket-type linkage structure mad a spring located in the middle of axis to realize an instant reset of the safety sleeve so as to ensure the needle tube not to be exposed in the air and further which uses some spring plates unevenly distributed on the inner wall of the needle base to realize a deflection and tilt of the self-destruction pressure seat and hence finally to ensure that the insulin needle cannot be reused for a result of safety and self-destruction operation of the insulin needle. The product is designed reasonably and tactfully and can be assembled automatically in the late process in order to improve the production efficiency and increase the stability of the product. The elastic resuming structure and automatic deflection structure in the product can be used in other fields.

Wherein, the numeral reference in the figures corresponds to the following element:
1 a needle base
2 A needle base protection cap
3 A self-destruction pressure seat
4 A safety clamping seat
5 A safety sleeve
6 A spring
7 A needle tube
8 A dialysis paper
9 A needle base substrate
10 A spring holding post
11 A spring plate
12 An upper separate space
13 A lower separate space
14 An annular limiting part
15 An annular limiting protruded part
16 An annular limiting step
17 An annular lump part
18 A round hole
19 A protruded clamping part
20 An inner screw
111 spring plate with a longer suspending part
112,113 spring plate with a shorter suspending part

DETAILED DESCRIPTION OF THE INVENTION

The following is the detailed description to the present invention in combination with the figures and embodiments.

Figure 1:
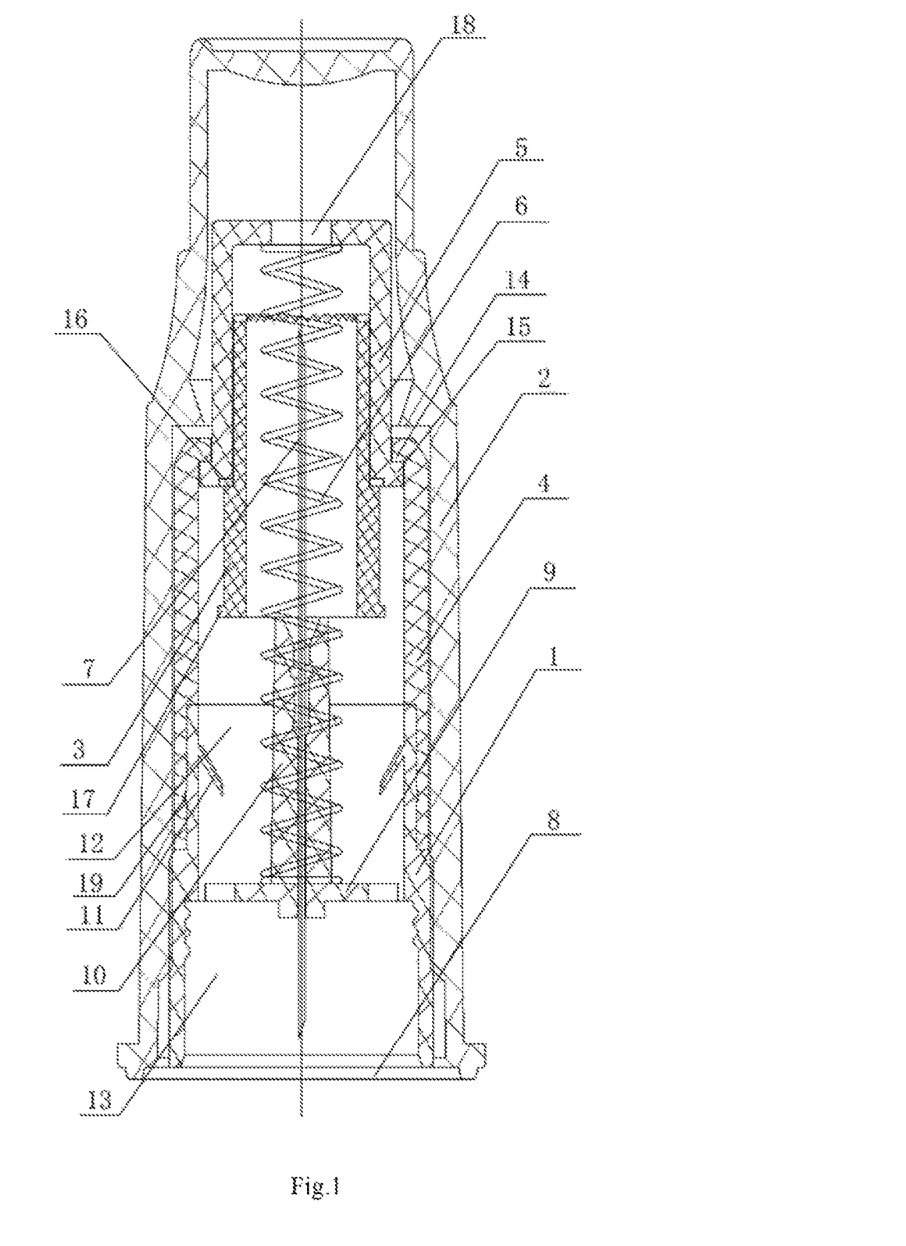
FIG. 1 is schematic view of the structure of the invention.

The invention proposes a disposable safety self-destruction insulin needle as shown in FIG. 1. It comprises a body of an insulin needle, its features distinguished from the prior art are provided as below: The body of the insulin needle is provided with a needle base 1 therein, which is generally in a form of cylinder. The needle base 1 has a hollow chamber which is provided with needle tube substrate 9 therein dividing the needle base into an upper separate space 12 and a lower separate space 13. The lower separate space 13 is provided on the inner wall with an inner screw 20. The needle tube substrate 9 is provided on the center position of the upper surface with a spring holding post 10 whose lower portion is located in the upper separate space 12. The needle tube substrate 9 is provided with a needle tube 7 which penetrates the needle tube substrate 9. One end of the needle tube 7 extends upward followed by penetrating the spring holding post 10 located on the centre position of the needle tube substrate 9, and the other end of the needle tube 7 extends towards inside of the lower separate space 13 followed by penetrating the needle tube substrate 9. The two ends of the needle tube 7 are both in form of a spine. The needle tube 7 is provided on the inner wall of the upper separate space 12 thereon with at least one spring plate 11. The spring plate is located diagonally on the inner wall of the inner chamber of the needle tube 7. One end of the spring plate is connected to the inner wall of the inner chamber of the needle tube 7 and the other end of the spring plate suspends in the air. The suspending end points to the upper surface of the needle tube substrate 9 at the place close to the center position. The spring holding post 10 is fit over by a spring 6 on the outside, one end of the spring 6 abuts downward against the upper surface of the needle tube substrate 9, and the other end of the spring 6 upward abuts against safety sleeve 5. The upper end of the needle base 1 is fitted over by a safety clamping seat 4, the lower end of which fits within the upper end of the needle base 1 each other. The upper end of the safety clamping seat 4 is provided with a safety sleeve 5 and the safety clamping seat 4 is shaped as a general cylinder and has a hollow chamber. The safety clamping seat 4 is provided on the inner edge of the upper opening with an annular limiting part 14. The safety sleeve 5 is shaped as a cylinder and has a hollow chamber and is provided on the outer edge of the lower opening with a annular limiting protruded part 15 cooperating to the annular limiting part 14. The annular limiting protruded part 15 is located within the chamber of the safety clamping seat 4 under the annular limiting part 14. The tipper end surface of the annular limiting protruded part 15 abuts downward against the lower end surface of the annular limiting part 14. The outer edge of the lower opening of the safety sleeve 5 limits and fits within the inner edge of the upper opening of the safety clamping seat 4. The spring 6 is fitted over by a self-destruction pressure base 3 which is shaped as a general cylinder and has a hollow chamber. The outer diameter of the upper portion of the self-destruction base 3 is smaller than the outer diameter of the lower portion of the self-destruction base 3. An annular step-shaped protrusion 16 is formed between the upper portion and the lower portion of the self-destruction pressure seat 3, the outer diameter of the lower portion of the self-destruction pressure seat 3 is larger than the diameter of the inner chamber of the safety sleeve 5, and the outer diameter of the upper portion of the self-destruction pressure seat 3 is smaller or equal to the diameter of the inner chamber of the safety sleeve 5. The upper portion of the self-destruction pressure seat 3 is located in the chamber of the safety sleeve 5. The annular step-shaped protrusion 16 has an end surface which abuts against the end surface of the lower end of the safety sleeve 5. The outer wall of the lower portion of the self-destruction pressure seat 3 is provided with an annular lump 17 cooperating with the spring plate 11. The vertical distance between the annular lump 17 and the needle tube 7 is larger than the vertical distance between the suspending part of the spring plate 11 and the needle tube 7. The upper end of the safety sleeve 5 is in a closed form, the closed end is provided with a round hole 18 therein. The diameter of the round hole 18 is smaller than the diameter of the upper end of the spring 6. The spring 6 has an upper end abutting upward against the inner surface of the upper end surface of the safety sleeve 5. The end surface of the lower end of the needle base 1 is covered with a dialysis paper.

In a preferred variant, the body of the insulin needle is provided with a protection cap of the needle base 2 the upper end surface of which is in a closed form and the lower end surface of which is in an opening form and which in sequence covers the safety sleeve 5 and the safety clamping seat 4 and the needle base 1.

In a preferred variant, the inner wall of the chamber of the needle tube 7 is provided with three spring plates 11 which are distributed on the same horizontal plane unevenly.

Figure 6:
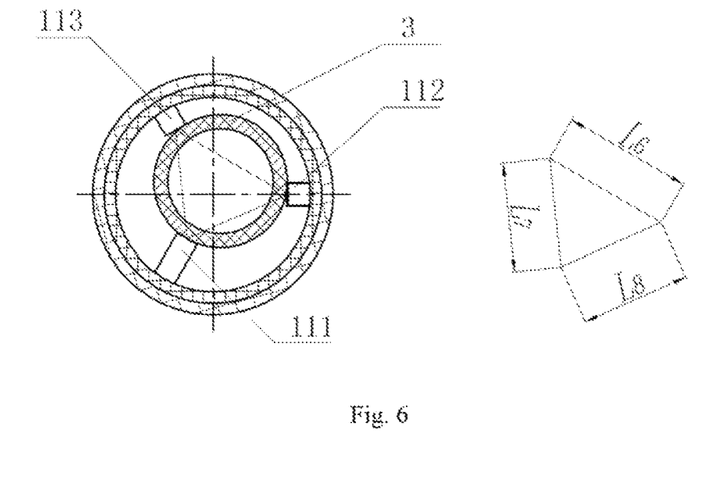
FIG. 6 is a view of three spring plates linked to form a triangle.

In a preferred variant, referring to FIG. 6, the needle tube 7 is provided on the inner wall of the chamber thereof with the three spring plates 111, 112, 113 adjacent to which the suspending parts are linked in a triangle. One edge L6 of the triangle is longer than the other two edges L7 and L8 of the triangle.

In a preferred variant, the needle base 1 fits within the safety clamping seat 4 each other, the outer wall of the needle base 1 closely fits, the needle base 1 is provided on the outer wall thereof with a protruded clamping part 19, the safety clamping seat 4 is provided on the inner wall of the chamber thereof with a recess cooperating with the protruded clamping part.

Figure 2:
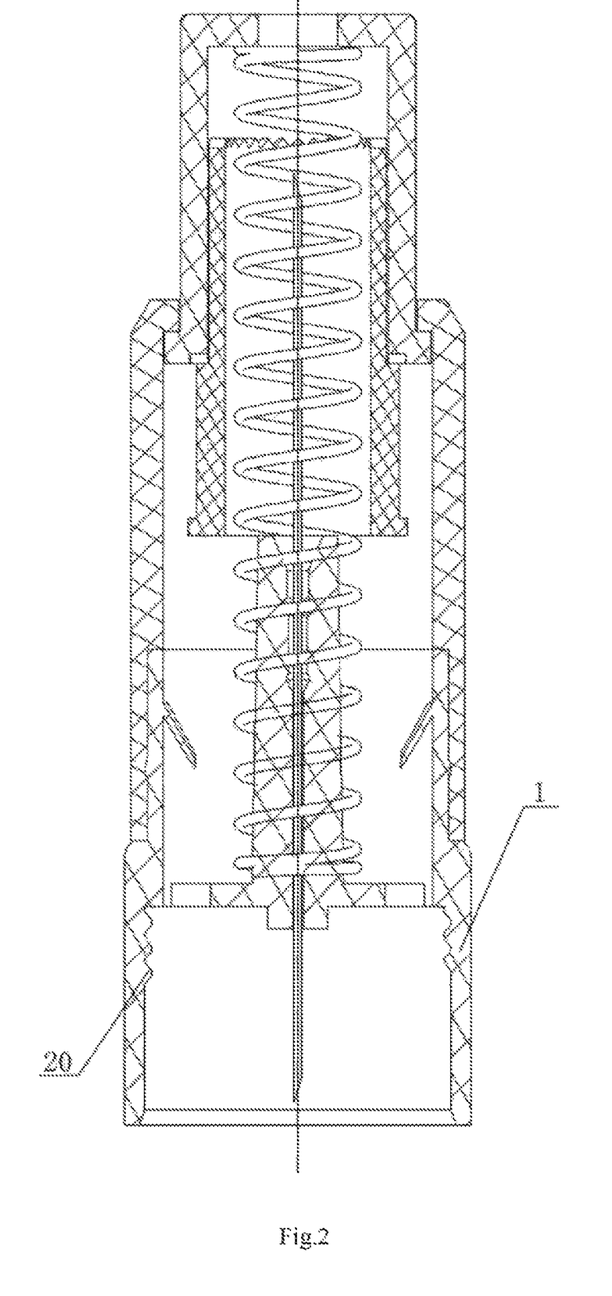
FIG. 2 is a view under a first step state of the invention.
Figure 3:
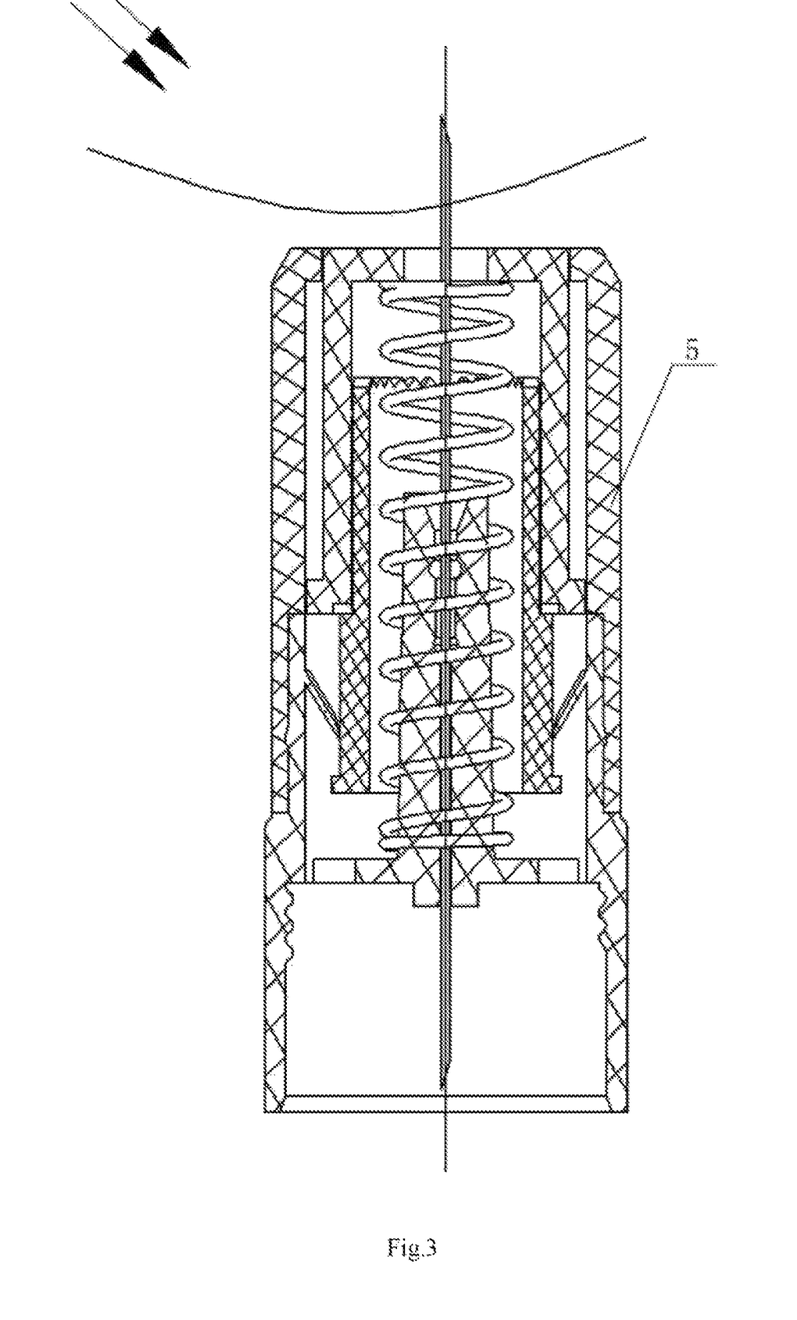
FIG. 3 is a view under a second step state of the invention.
Figure 4:
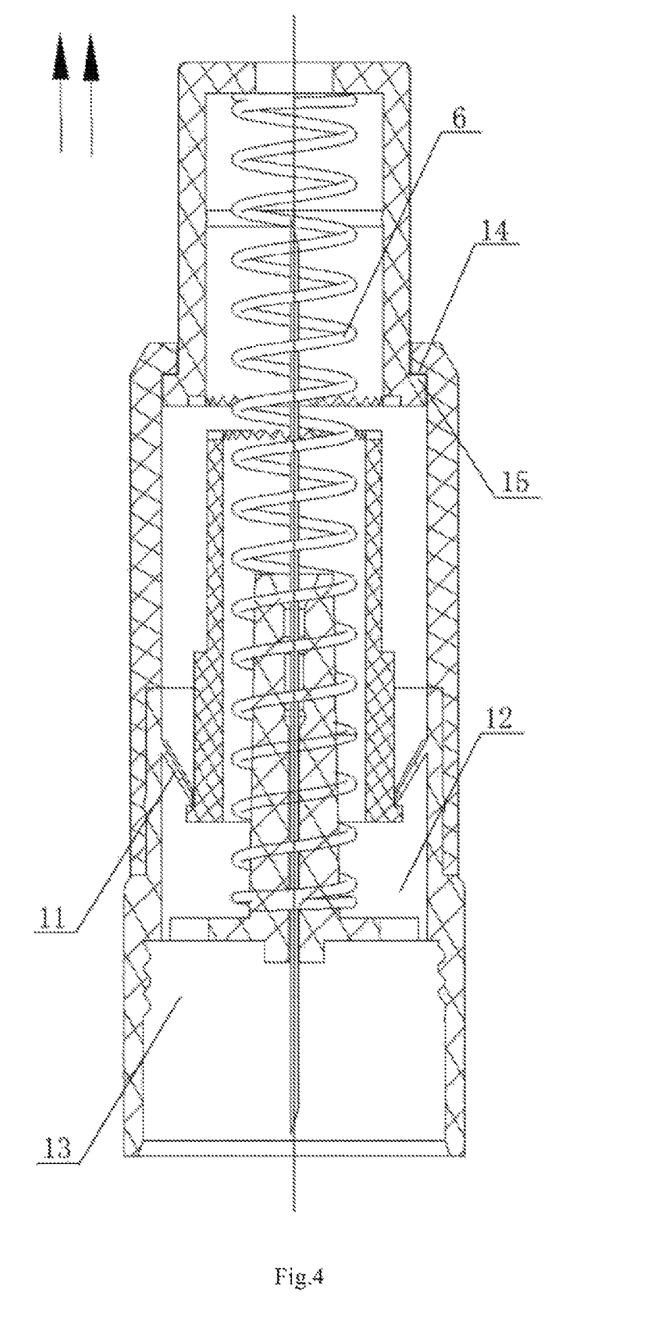
FIG. 4 is a view under a third step state of the invention.
Figure 5:
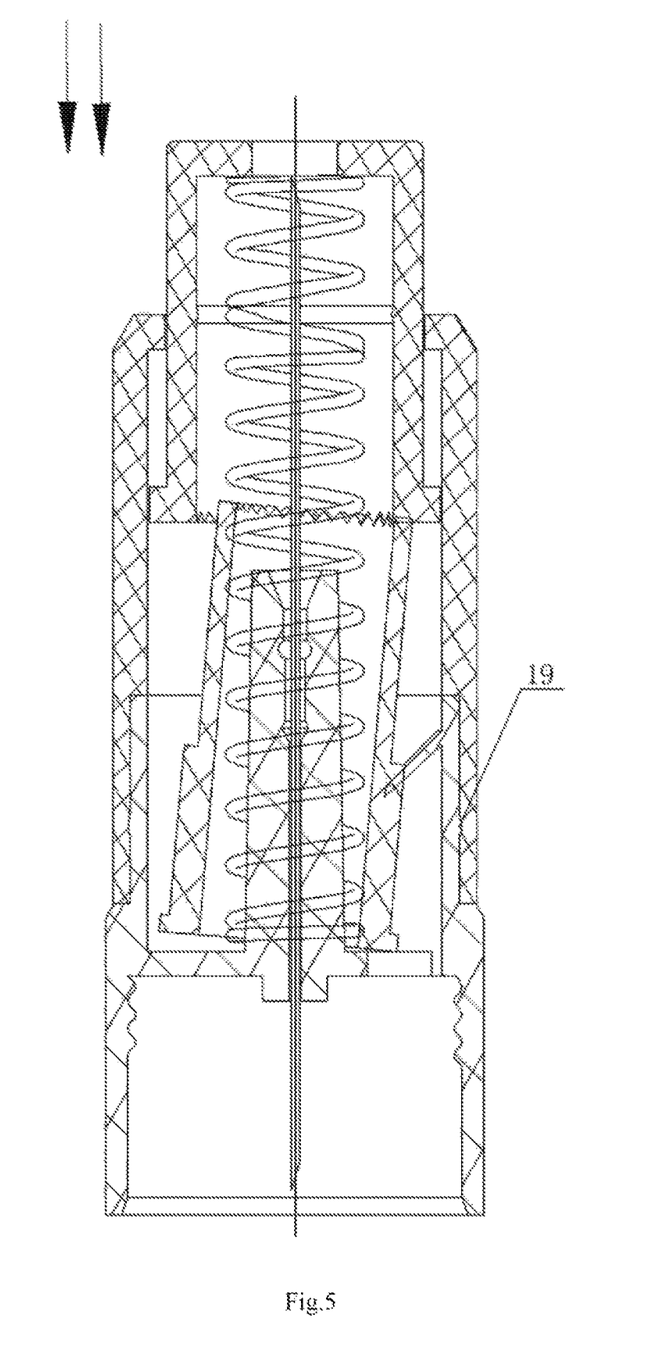
FIG. 5 is a view under a fourth step state of the invention.

In the practical use, as seen in FIG. 2, during step 1, the outer screw on the front end of the insulin needle cooperates by screwing in with the inner screw 20 on the back end of the insulin needle, the lower end of the needle tube 7 penetrates the insulin pen and then the needle base protection cap 2 is removed at the same time when the safety sleeve 5 on the top part of the insulin needle is exposed. As shown in FIG. 3, during step 2, the protection sleeve 5 is pushed against the skin of the patient and naturally is pressed down so that the safety sleeve 5 is forced to move inward to the chamber of the safety clamping seat 4 until the safety sleeve 5 completely is caught in ile safety clamping seat 4. As the safety sleeve 5 moves down the self-destruction pressure seat 3 is carried together with it to move down. During the movement, when the annular lump part 17 on the outer wall of the self-destruction pressure seat 3 comes into contact with the spring plate 11 it will by the way press the spring plate 11 to expand outward. During the expansion of the spring plate 11, the annular lump part 17 goes beyond the suspending end of the spring plate 11 and then therefore the force applied on the spring plate 11 disappears and the spring plate 11 resumes to its original state. In so doing the annular lump part and its under part of the self-destruction pressure seat 3 are limited between the spring plate 11 and the needle tube substrate 9. During the movement of the safety sleeve 5, the upper end of the needle tube can be exposed in the air after penetration of the round hole 18 and then by the way stabs into the skin of the patient so as to inject. During step 3, as seen in the FIG. 4, after injection, the head of the needle tube can be pulled backward and hence the resistance applied on the safety sleeve 5 by the skin disappears, therefore under the returning force of the spring 6, the safety sleeve 5 instantly springs out upward so that the needle tube exposed in the air is completely covered to ensure the needle tube cannot be exposed and the safe operation of the insulin is realized. Under interaction between the annular limiting part 14 and the annular protruded limiting part 15, in combination with the upward returning force of the spring 6, the lower end of the safety sleeve 5 clamps the upper end of the safety clamping seat each other so as to realize the positioning of the safety sleeve 5. During the upward movement of the safety sleeve 5, it can carry the self-destruction 3 together to move upward due to the clamping structure provided between the inner wall of the safety sleeve 5 and the outer wall of the self-destruction pressure seat 3. However, during the movement, the annular lump part 17 on the outer wall of the self-destruction pressure seat 3 no longer goes beyond the suspending part of the spring plate 11. During step 4, as seen in FIG. 5, since the distribution of the spring plates is uneven and the distance between two of them is larger than the other two of them, the instant resistance applied on the annular protruded part 17 is different. At the time of no movement of the self-destruction pressure seat due to resistance, the returning force of the spring continues to apply on the upper end of the safety sleeve 5. As for the returning force, the self-destruction pressure seat 3 instantly go away from the safety sleeve 5. When the self-destruction pressure seat 3 completely goes away from the safety sleeve 5, under unsymmetrical resistance, the self-destruction pressure seat 3 can instantly tilt to one side because the distribution of the spring plates is uneven so that the force applied on the annular protruded part 17 instantly by the spring plate is different and therefore, when the annular lump part 17 comes into contact with the spring plate 11, the angle and the depth with which the spring plate penetrates are different. Therefore, under the returning force by the spring plate, the whole self-destruction pressure seat 3 tilt to one side so that the self-destruction pressure seat deflects from the center. When the safety sleeve is pressed down again, the upper end of the self-destruction pressure seat 3 abuts upward against the lower end of the safety sleeve, so that the safety sleeve cannot be pressed again. Therefore, reusing the disposable safety self-destruction insulin needle is thoroughly prevented and finally the effect of safe self-destruction of the insulin needle is realized.

The above-mentioned teaching is a description of the invention in combination with the preferred examples and cannot be taken as a limitation to the invention. Those skilled in the art can make some substitutes or derivation based on the idea of the invention without departing from the scope of the invention.

The invention claimed is:

1. A disposable safety self-destruction insulin needle, comprising: a body of an insulin needle, wherein the body of the insulin needle is provided with a needle base therein, which is generally in a form of a cylinder and which has a hollow chamber which is provided with a needle tube substrate therein dividing the needle base into an upper separate space and a lower separate space that is provided on an inner wall with an inner screw thread, the needle tube substrate is provided on a center position of an upper surface with a spring holding post whose lower portion is located in the upper separate space, the needle tube substrate is provided with a needle tube which penetrates the needle tube substrate, one end of the needle tube extends through the spring holding post located on the centre position of the needle tube substrate, the other end of the needle tube extends towards inside of the lower separate space, two ends of the needle tube are both in a form of a spine, the needle tube is provided on an inner wall of the upper separate space thereon with at least three spring plates which are located diagonally on an inner wall of an inner chamber of the needle tube, and wherein one end of each spring plate is connected to the inner wall of the inner chamber of the needle tube, and the other end of each spring plate suspends in the air, a suspending part of each spring plate points to the upper surface of the needle tube substrate at a place close to the center position of the upper surface, the spring holding post is fitted over by a spring on the outside, one end of the spring abuts downward against the upper surface of the needle tube substrate, the other end of the spring upward abuts against a safety sleeve, an upper end of the needle base is fitted over by a safety clamping seat, the lower end of safety clamping seat fits in/over the upper end of the needle base, the upper end of the safety clamping seat is provided with the safety sleeve and the safety clamping seat is shaped as a general cylinder and has a hollow chamber and is provided on an inner edge of an upper opening with an annular limiting part, the safety sleeve is shaped as a cylinder and has a hollow chamber and is provided on an outer edge of a lower opening with an annular limiting protruded part cooperating to the annular limiting part, the annular limiting protruded part is located within the chamber of the safety clamping seat under the annular limiting part, a top planar surface of the annular limiting protruded part is directly connected and adjacent to a bottom planar surface of the annular limiting part, the outer edge of the lower opening on a lower portion of the safety sleeve limit and fit within the inner edge of the upper opening of the safety clamping seat, the spring is fitted over by a self-destruction pressure seat which is shaped as a general cylinder and has a hollow chamber, an outer diameter of the upper portion of the self-destruction pressure seat is smaller than an outer diameter of the lower portion of the self-destruction pressure seat, an annular step-shaped protrusion is formed between an upper portion and a lower portion of the self-destruction pressure seat, the outer diameter of the lower portion of the self-destruction pressure seat is larger than the diameter of the inner chamber of the safety sleeve, the outer diameter of the upper portion of the self-destruction pressure seat is smaller or equal to the diameter of the inner chamber of the safety sleeve, the upper portion of the self-destruction pressure seat is located in the chamber of the safety sleeve, the annular step-shaped protrusion has a planar surface which abuts against a most bottom planar surface of the safety sleeve, the outer wall of the lower portion of the self-destruction pressure seat is provided with an annular lump cooperating with the spring plate, wherein a horizontal distance between the annular lump and the needle tube is larger than a horizontal distance between the suspending part of the each spring plate and the needle tube, such that when the annular lump gets pushed beyond the suspending part of the spring plate, the annular lump gets limited between the each spring plate and the needle tube substrate, wherein the at least three spring plates are distributed at unequal distances from each other on the inner wall of the needle base and are distributed around the spring holding post, and at least three spring plates exert unsymmetrical resistance on different sections of the annular lump, such that the self-destruction pressure seat is deflected and tilted until an upper portion of the self-destruction pressure seat abuts against a lower portion of the safety sleeve and the annular lump gets limited between the spring plate and the needle tube substrate, wherein the upper end of the safety sleeve is in a closed form, a closed end is provided with a round hole therein, the diameter of the round hole is smaller than the diameter of an upper end of the spring, the spring has the upper end abutting upward against an inner surface of an upper end surface of the safety sleeve, an end surface of a lower end of the needle base is covered with a dialysis paper, wherein the spring holding post is surrounded by the spring, wherein the lower separate space is below the needle tube substrate.

2. The disposable self-destruction safety insulin needle according to claim 1, wherein the body of the insulin needle is provided with a protection cap of the needle base, the upper end surface of which is in a closed form and the lower end surface of which is in an opening form and which in sequence covers the safety sleeve and the safety clamping seat and the needle base.

3. The disposable self-destruction safety insulin needle according to claim 1, wherein the inner wall of the chamber of the needle tube is provided with the three spring plates distributed at varying distances from each other and distributed on a same horizontal plane, and the three spring plates exert unsymmetrical resistance on different sections of the annular lump to deflect and tilt the self-destruction pressure seat.

4. The disposable self-destruction safety insulin needle according to claim 3, wherein the needle tube is provided on the inner wall of the chamber with the three spring plates, three suspending parts of the three spring plates are linked to form a triangle within the inner wall of the chamber, one edge of the triangle is longer than the other two edges.

5. The disposable self-destruction safety insulin needle according to claim 1, wherein the needle base fits within the safety clamping seat with each other, the outer wall of the needle base closely fits, the needle base is provided on the outer wall thereof with a protruded clamping part, the safety clamping seat is provided on the inner wall of the chamber thereof with a recess cooperating with a protruded clamping part.

\* \* \* \* \*

UNITED STATES PATENT AND TRADEMARK OFFICE
CERTIFICATE OF CORRECTION

PATENT NO. : 9,931,476 B2
APPLICATION NO. : 14/929407
DATED : April 3, 2018
INVENTOR(S) : Hongjie Zhang et al.

Page 1 of 1

It is certified that error appears in the above-identified patent and that said Letters Patent is hereby corrected as shown below:

On the Title Page

Item (73), The Assignee should read (--Berpu Medical Technology Co., Ltd.--) instead of Beipu Medical Technology Co.,Ltd.

Signed and Sealed this
Second Day of July, 2019

Andrei Iancu
*Director of the United States Patent and Trademark Office*